US010993835B2

(12) United States Patent
Claret et al.

(10) Patent No.: US 10,993,835 B2
(45) Date of Patent: *May 4, 2021

(54) DEVICE FOR PACKAGING AND DISPENSING A SUBSTANCE FOR OPHTHALMIC USE

(71) Applicant: Horus Pharma, Saint-Laurent-du-Var (FR)

(72) Inventors: Martine Claret, Nice (FR); Pierre Roy, Paris (FR)

(73) Assignee: Horus Pharma

( * ) Notice: Subject to any disclaimer, the term of this patent is extended or adjusted under 35 U.S.C. 154(b) by 226 days.

This patent is subject to a terminal disclaimer.

(21) Appl. No.: 16/033,426

(22) Filed: Jul. 12, 2018

(65) Prior Publication Data

US 2018/0318130 A1 Nov. 8, 2018

Related U.S. Application Data

(63) Continuation of application No. 14/377,241, filed as application No. PCT/EP2013/052587 on Feb. 8, 2013, now Pat. No. 10,022,266.

(30) Foreign Application Priority Data

Feb. 9, 2012 (FR) ........................ 1251246

(51) Int. Cl.
*A61F 9/00* (2006.01)
*A61M 35/00* (2006.01)
*B29D 22/00* (2006.01)

(52) U.S. Cl.
CPC .......... *A61F 9/0026* (2013.01); *A61F 9/0008* (2013.01); *A61M 35/003* (2013.01);
(Continued)

(58) Field of Classification Search
CPC ............ B65D 83/0011; B65D 83/0022; B65D 83/0027; B65D 83/0033; B65D 83/0038;
(Continued)

(56) References Cited

U.S. PATENT DOCUMENTS 6,354,469 B1 * 3/2002 Pozzi ................. B05B 11/0037
222/189.09
2007/0219527 A1 * 9/2007 Barron .............. A61M 25/0075
604/523

(Continued)

FOREIGN PATENT DOCUMENTS

| FR | 2873358 A1 | 1/2006 |
| FR | 2941682 A1 | 8/2010 |
| WO | 2009073482 A1 | 6/2009 |

OTHER PUBLICATIONS

International Search Report and Written Opinion for Application No. PCT/EP2013/052587 dated May 14, 2013.

*Primary Examiner* — Tatyana Zalukaeva
*Assistant Examiner* — Jessica R Arble
(74) *Attorney, Agent, or Firm* — Lerner, David, Littenberg, Krumholz & Mentlik, LLP

(57) ABSTRACT

Device for packaging and dispensing drops of a substance for ophthalmic use, generally fluid, semi-fluid or in suspension, emulsion or oily solution including a dispensing accessory with a first valve made of an elastomer material that allows the substance to pass through when the dispensing accessory is stressed, without allowing outside air to pass through in the opposite direction when the dispensing accessory is relaxed, characterized in that the first valve is covered by a layer of Parylene.

17 Claims, 9 Drawing Sheets

(52) U.S. Cl.
CPC ..... *B29D 22/00* (2013.01); *A61M 2205/3331* (2013.01); *A61M 2205/7536* (2013.01); *Y10T 29/49405* (2015.01)

(58) Field of Classification Search
CPC . B65D 83/0044; B65D 83/005; A61F 9/0026; A61F 9/0008; A61M 35/003; A61M 2205/3331; A61M 2205/7536; B29D 22/00
See application file for complete search history.

(56) References Cited

U.S. PATENT DOCUMENTS

| | | |
|---|---|---|
| 2008/0181930 A1 | 7/2008 | Rodstrom et al. |
| 2008/0302828 A1* | 12/2008 | Pozzi ................. B65D 47/2056 222/189.09 |
| 2010/0226962 A1 | 9/2010 | Rodstrom et al. |
| 2011/0278323 A1 | 11/2011 | Pozzi et al. |
| 2012/0067926 A1* | 3/2012 | Ishikawa ............ B65D 47/2068 222/422 |

* cited by examiner

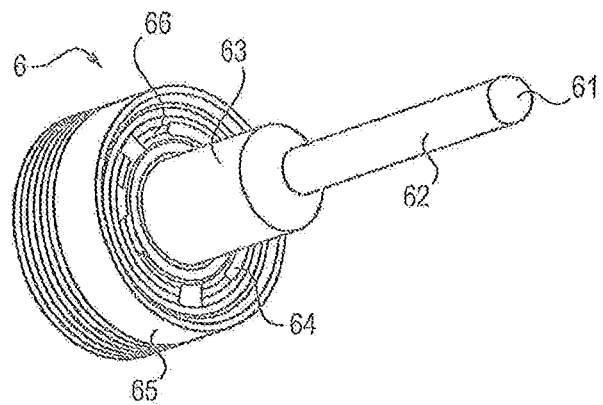
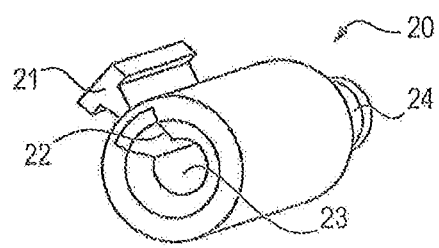
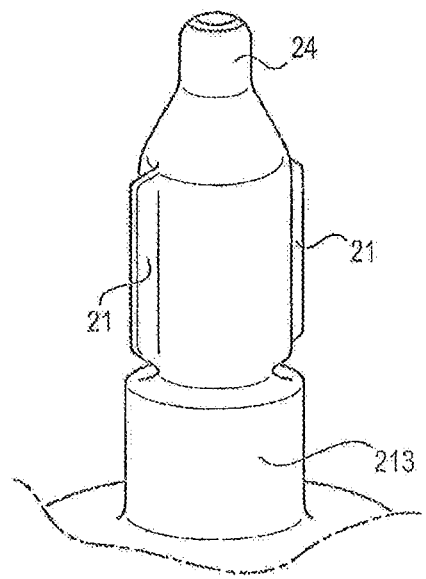
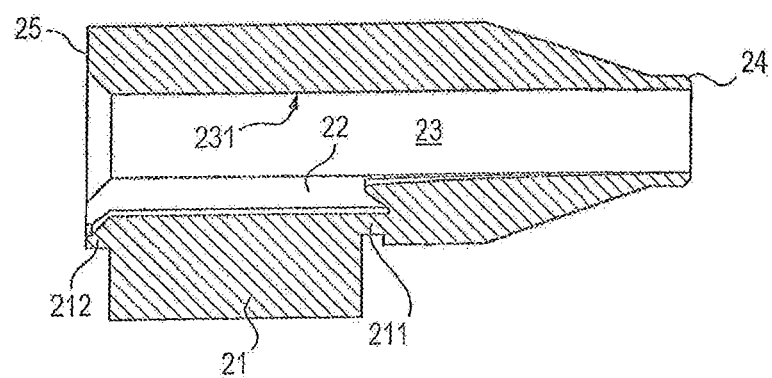

DEVICE FOR PACKAGING AND DISPENSING A SUBSTANCE FOR OPHTHALMIC USE

CROSS-REFERENCE TO RELATED APPLICATIONS

The present application is a continuation of U.S. application Ser. No. 14/377,241, filed Dec. 2, 2014 which is a national phase entry under 35 U.S.C. § 371 of International Application No. PCT/EP2013/052587, filed on Feb. 8, 2013, published in French, which claims priority from French Patent Application No. 1251246, filed Feb. 9, 2012, the disclosures of which are incorporated by reference herein.

FIELD OF THE INVENTION

The invention relates to a device for packaging and dispensing drops of a product for ophthalmic use, generally fluid, semi-fluid or, emulsion or oily solution.

There are existing devices for packaging and dispensing of classic structure which hold and dispense a product in the form of doses or drops or in any other form, and retain its cleanness or its sterility throughout its use, without the addition of preservatives.

These devices are used especially in the pharmaceutical, cosmetic and food fields, and for some more particularly in the ophthalmologic field.

Within the scope of ophthalmology, delivering one or more drops of product for the great majority of this type of devices is done by squeezing the bottle containing the product between the thumb and the index finger.

The majority of ophthalmic solutions, irrespective of their function (treating an ocular condition, cicatrisation, hydration, etc.), are sold in a polyethylene packaging vial equipped with a drop-counting nozzle for dispensing directly into the eye.

All vials of this type pose a protection problem against proliferation of microbes, which risks causing microbiological contamination of the eye of the patient when the drops are dispensed.

To rectify this, it is conventional to use antimicrobial preservative agents introduced as a mixture to the solution. But such agents, benzalkonium chloride for example, have the major disadvantage of being aggressive to eyes.

Several solutions for vials have been developed or are under development for avoiding the use of preservatives and retain the sterility of the product during its use.

The solutions described employ either an antibacterial filter, or systems comprising ball-and-spring valves, or anti-bacterial materials, or more particularly elastomer valves.

Document FR 2873358 describes a device in which the product is expelled via a flexible nozzle with which the container is fitted. The flexible nozzle forms a small reservoir called a dispensing chamber and is located between two non-return valves. A first valve is placed at the level of the reservoir or medication vial and opens in the direction of the dispensing chamber. The second valve, of annular form, is placed after the dispensing chamber and opens in the direction of the dispensing end of the nozzle. Under the effect of pressure created by squeezing the walls of the flexible nozzle at the level of the dispensing chamber, the liquid is expelled towards the opening of the device via the second valve. When the squeezing pressure is relaxed, under the effect of its elasticity, the dispensing chamber regains its initial form and opens the first valve by letting a new dose of product fill the dispensing chamber, while the second valve closes. The device also comprises a valve at the level of the air intake filter. These valves are made of silicone.

For this latter solution, silicone elastomers are often used because of their properties recognised for pharmaceutical usage (materials inscribed in the pharmacopoeia).

Analogs of prostaglandin are medications used exclusively in ophthalmology for treating glaucoma, a condition often linked to excessively high intraocular pressure (IOP).

Prostaglandin in particular makes for easier flow of the aqueous humour via uveoscleral flow. Research has revealed a molecule which reproduces this effect locally. These medications were sold for the first time in 1996. Latanoprost (Xalatan, by Pfizer) was the first prostaglandin developed for treating glaucoma and proves efficacious for reducing IOP with daily application at bedtime. Normally during the day the aqueous humour flows mostly through the trabeculum and a little via the uveoscleral channel. However, during the night it mostly uses the uveoscleral channel. In a low dose, latanoprost increases evacuation via the uveoscleral channel for a long period and needs a single daily application only.

Other similar medications of prostaglandin of the same category are travoprost (Travatan, by Alcon), bimatoprost (Lumigan, by Allergan) and tafluprost (Taflotan, by Santen).

It has been noted that in a device for packaging and dispensing product such as described in document FR873358, the product for ophthalmic use comprising an analog of prostaglandin is unstable. In particular, its composition is greatly modified and its analog concentration of prostaglandin decreases.

In the prior art there is no device for packaging and dispensing product drops for ophthalmic use comprising an analog of prostaglandin.

In particular in the prior art there is no device for packaging and dispensing product drops for ophthalmic use comprising an analog of prostaglandin without preservative and ensuring the sterility of the product.

There is no such device which ensures stability of such a product.

GENERAL PRESENTATION OF THE INVENTION

An aim of the invention is to provide a dispensing accessory for a device for packaging and dispensing of a product for ophthalmic use, in particular a product occurring within the scope of treatment against glaucoma, comprising an analog of prostaglandin, a product comprising a corticoid or a product comprising a non-steroidal anti-inflammatory, which dispenses clean or sterile drops of product frequently and repetitively, and which ensures better packaging of the product.

In this way, a device is provided for packaging and dispensing drops of a product for ophthalmic use, generally fluid, semi-fluid or in suspension, emulsion or oily solution, comprising a dispensing accessory comprising a first valve made of elastomer material allowing the product to pass through when the dispensing accessory is stressed without allowing outside air to move in the reverse direction when the dispensing accessory is relaxed, characterized in that the first valve is covered in a layer of parylene.

The invention is advantageously completed by the following characteristics, taken singly or in any of their technically possible combinations:
- a container intended to contain the product and dispense it, the dispensing accessory being mounted on the container and the first valve enabling the exit of the product from the container when the dispensing accessory is stressed without allowing outside air to enter the container when the dispensing accessory is relaxed, a renewal and filtration assembly for air entering the container after dispensing a portion or dose of product, comprising a second valve made of elastomer material and covered in a layer of parylene, allowing outside air to enter said container when the dispensing accessory is relaxed without allowing the product or substantially the air contained inside the container to exit when the dispensing accessory is stressed, the second valve has a form comprising:
a circular form substantially plane having two faces, a first face being turned towards the interior of the container and delimited by an outer rim, and
a protuberance extending over a central area of the circular form delimited by an inner diameter, engaged with the circular form, extending perpendicularly to the circular form on either side of the circular form,
the first valve has a hat shape, comprising:
a central cylindrical form, and
a peripheral circumferential protuberance,
the first and/or second valve(s) has (have) a substantially plane general circular form delimited by an outer rim and is (are) adapted to allow passage of the product:
by deformation at the level of a central area, the outer rim of the valve being held in position by forces applied to either side of the latter, or
by deformation of the outer rim, a central area of the valve being held in position by forces applied on either side of the latter,
the thickness of the first and/or second valve(s) increases between the central area and the outer rim,
the first and/or second valve(s) at rest has a curve profile and/or having at least one angle,
the form of the first and/or second valve(s) has at least one circumferential protuberance extending over at least one of the faces of the first and/or of the second valve(s),
the first valve has a substantially plane annular form delimited by:
an inner diameter between 5 and 10 mm and
an outer diameter of between 11 and 20 mm, the outer diameter having a thickness (e) of between 0.25 and 2.5 mm,
the elastomer material of the first and/or second valve(s) is silicone,
the elastomer material of the first and/or second valve(s) is thermoplastic elastomer with a polyolefin base, or styrene-based thermoplastic elastomer or thermoplastic polyurethane,
the dispensing accessory is a dispensing accessory of calibrated drops comprising:
a supple membrane stress of which causes dispensing of the product,
a dispensing chamber of the product delimited at least by:
a first portion of a periphery of a rigid core, and
a part of an elastically deformable supple membrane located opposite the first portion, the supple membrane extending about the rigid core, the first valve made of elastomer material allowing passage of the product into the dispensing chamber when the supple membrane is stressed without allowing outside air to move in the reverse direction when the supple membrane is relaxed,
form-holding means of the supple membrane, relative to at least one second portion of the periphery of the rigid core, the form-holding means comprising:

at least one rigid piece attached to the supple membrane and extending opposite the second portion of the periphery of the rigid core, the rigid piece being located between the supple membrane and the second portion of the periphery of the rigid core, or a rigid piece attached to a part of the supple membrane extending opposite the second portion of the periphery of the rigid core, the part of the supple membrane being located between the rigid piece and the second portion of the periphery of the rigid core, or an assembly of the supple membrane with a surface of the second portion of the periphery of the rigid core by adhesion or welding, the dispensing chamber has a cross-section of general trapezoid form, and/or the part of the supple membrane delimiting the dispensing chamber forms a generally prismatic piece which comprises two ends, each having an area of lesser thickness.

The invention also relates to use of such a device for packaging and dispensing of calibrated drops of a product for ophthalmic use, in particular comprising an analog of prostaglandin, a corticoid or a non-steroidal anti-inflammatory.

The invention further relates to a process for manufacture of such a device, comprising:
moulding of a first and/or second valve(s) made of elastomer,
parylene processing of the first and/or second valve(s) made of elastomer to cover its surface with a coating of parylene
mounting of the device with the resulting first and/or second valve(s)

PRESENTATION OF FIGURES

Other characteristics and advantages of the invention will emerge from the following description of an embodiment. In the appended drawings:

FIG. 1a, respectively 1b, is a view in longitudinal section illustrating a first, respectively a second, embodiment of the device for packaging and dispensing a product for ophthalmic use comprising a dispensing accessory according to the invention;

FIG. 2 is a three-dimensional view of a central piece forming a rigid core of the dispensing accessory of FIGS. 1a and 1b;

FIG. 3a, respectively 3b, is a three-dimensional view of a supple membrane of the dispensing accessory illustrating the first, respectively second, embodiment of the device according to the invention;

FIG. 4a, respectively 4b, is a view in longitudinal section of the supple membrane of FIG. 3a, respectively 3b;

Figure 11A:
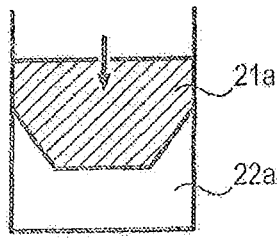
Figure 11B:
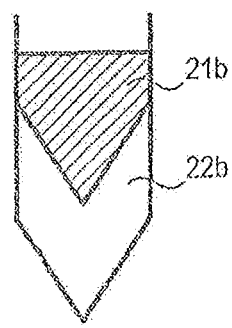
Figure 11C:
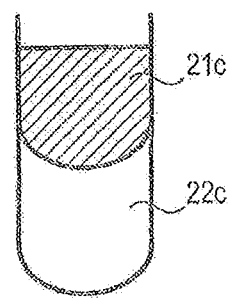

FIGS. 11a to 11c schematically illustrate several variant embodiments for filling a dispensing chamber of the dispensing accessory illustrating the device according to the invention, FIGS. 12a to 12h schematically illustrate several variant embodiments of a first valve illustrating the device according to the invention, FIGS. 13a to 13g schematically illustrate several variant embodiments of a second valve illustrating the device according to the invention.

FIGS. 14a to 14c and 15a to 15c illustrate results of analysis by chromatography for a valve according to the prior art and a valve illustrating a device according to the invention.

DESCRIPTION OF THE INVENTION

Examples Illustrating Embodiments of the Device

Figure 1A:
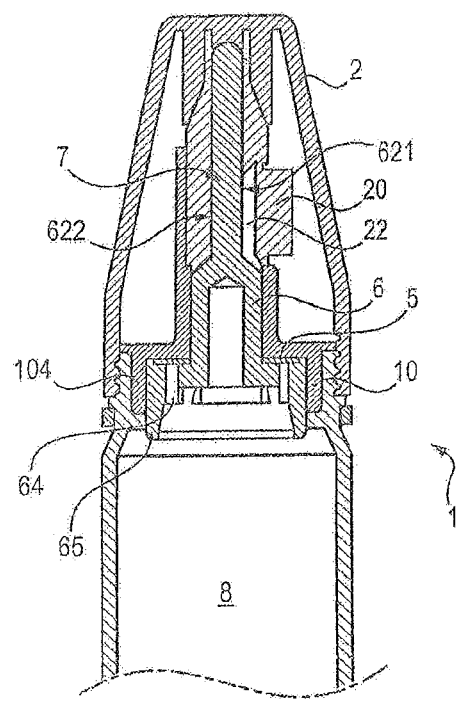
Figure 1B:
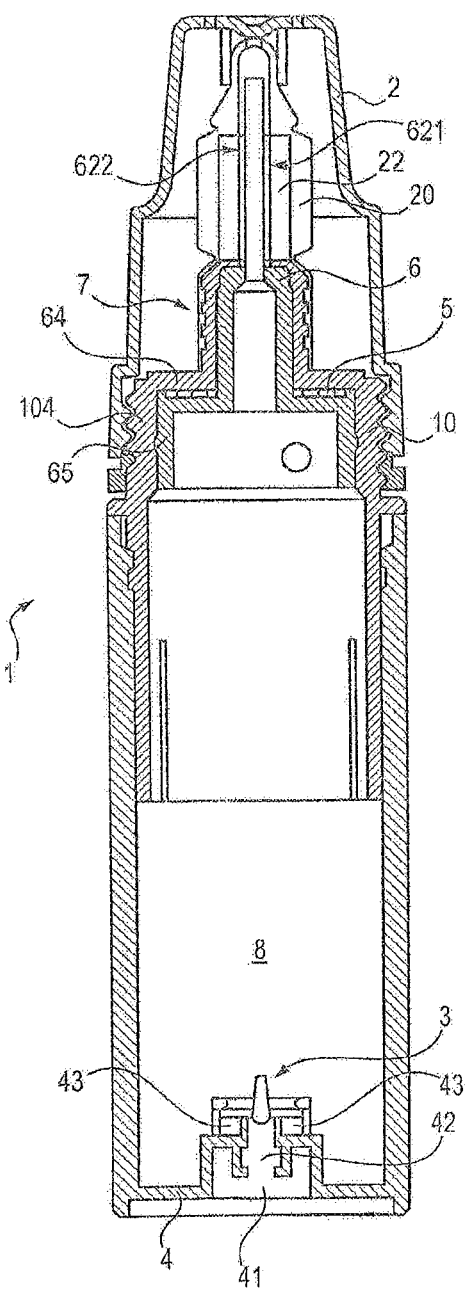

In reference to FIGS. 1a and 1b, these describe a device for packaging and dispensing product for ophthalmic use 1 comprising a dispensing accessory 7. FIG. 1a, respectively 1b, illustrates a first, respectively a second, embodiment of a device. The characteristics of these two embodiments can be combined.

The device for packaging and dispensing 1 comprises a container 8. The container 8 is closed at one of its ends by a base 4 comprising means for air intake and filtration. These air intake and filtration means introduce air to the enclosure of the container 8 as the product initially contained in said enclosure is dispensed. As the incoming air is being filtered, this ensures the cleanness or sterility of the product remaining in the enclosure of the container 8.

Such means are for example described in more detail in document FR 2772007.

At one end opposite that comprising the base 4, the container 8 has an opening and the dispensing accessory 7 obstructing said opening. The dispensing accessory 7, and illustrating the first, respectively second embodiment of FIG. 1a, respectively 1b, comprises a central piece forming a rigid core 6 on which coaxially fits a supple membrane 20, a second rigid piece 10 comprising at least one growth 101, and a first valve 5. A removable stopper 2 completes the device for packaging and dispensing 1 by covering the dispensing accessory 7 to protect it when the device 1 is not in use.

The rigid core 6, shown in FIG. 2 in three dimension, extends longitudinally and comprises at one end a base 65 open to the enclosure of the container 8 when said base 65 is mounted tightly in the opening of said container 8. A shoulder 66 connects the base 65 to a first section 63. The shoulder 66 comprises an annular cavity at the base of which continuous orifices 64 are arranged. Here, there are four orifices 64 and are distributed uniformly over a circumference. The number and form of these orifices 64 can vary and be adapted to the product for ophthalmic use which is intended to be contained in the container 8 and be dispensed by way of the dispensing accessory 7. The orifices 64 form a passage between the interior of the base 65 and the exterior. The first section 63 extends longitudinally via a second section 62 of cross-section smaller than a cross-section of the first section 63. The second section 62 extends longitudinally as far as an opposite end 61 of the rigid core 6 relative to the base 65.

Examples of Supple Membrane

The supple membrane 20 illustrating the first embodiment is shown in FIG. 3a according to a three-dimensional view and FIG. 4a according to a view in section. It has a substantially cylindrical form and extends longitudinally between an end 25 and an end 24. The supple membrane 20 comprises a coaxial recess 23 of cylindrical form and extending longitudinally between the two ends 24 and 25.

Also, extending from the end 25 over around a first half, the supple membrane 20 comprises at least one chamber 22, called a dosage membrane, arranged in a thickness of the wall of the membrane and open to the recess 23. Opposite this dispensing chamber 22, the recess 23 comprises a surface 231. In reference to FIG. 9a, the dispensing chamber 22 has, in cross-section, an overall trapezoid form whereof a small base forms the opening in the recess 23 which extends along a first portion of a periphery of the recess 23. The surface 231 opposite extends over a second portion of the periphery of the recess 23 complementary to the first portion of the periphery of said recess 23.

The dispensing chamber 22 is delimited centrifugally by a part 21 of the supple membrane. This part 21 forms a piece generally of prismatic form. It is elastically deformable and comprises at each of its ends an area of lesser thickness 211, 212. In this way, pressing on the part 21 enables quasi-vertical displacement of the prismatic piece in the dispensing chamber 22 and reduces force to be provided when the device is used to distribute a dose or drop of product contained in the enclosure of the container 8.

Figure 4B:
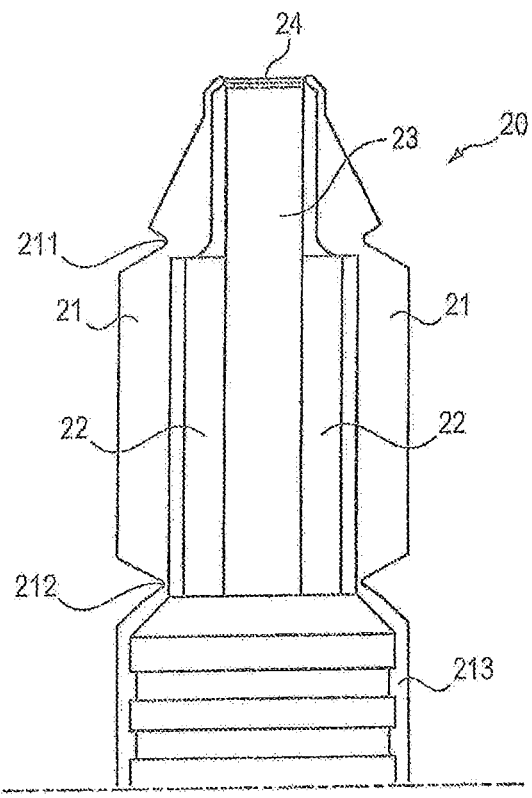

The supple membrane 20 illustrating the second embodiment is shown in FIG. 3b according to a three-dimensional view, in FIG. 4b according to a view in section. It differs from the supple membrane illustrating the first embodiment in that it comprises two diametrically opposed dosing chambers 22. The second rigid piece 10 is inside the supple membrane 20 which when mounted is fitted onto the rigid core 6 and onto the second piece 10. The supple membrane 20 comprises a skirt 213 covering an intermediate part 108 of the second piece 10. The growth 101 is then sandwiched between the supple membrane 20 and a portion of the second section 62 of the rigid core 6. The supple membrane 20 is glued or welded onto an outer surface of the growth 101, ensuring that it cannot deform during use.

Also, between the areas 211 and 212 the recess 23 has a greater diameter than between the area 211 and the end 24. The area corresponding to the dosing chambers 22 is therefore included in the recess 23. As in the first embodiment, the dosing chambers 22 are always limited both by the part 21 and by a portion of the second section 62. However, the two other walls extending longitudinally from the dispensing chamber are constituted by portions of lateral walls of two growths 101 from the second rigid piece 10.

Examples of Second Rigid Piece

Figure 5:
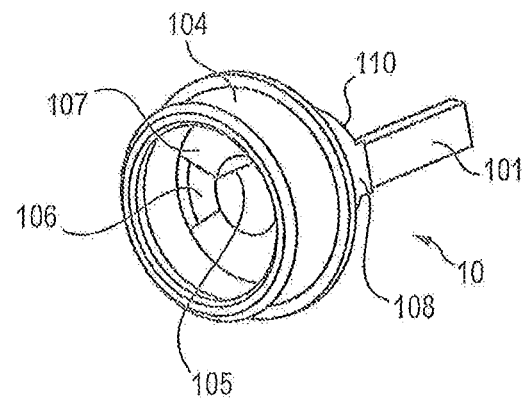
FIG. 5, is a three-dimensional view of an outer piece forming a second rigid piece illustrating the first embodiment of the device according to the invention.
Figure 6A:
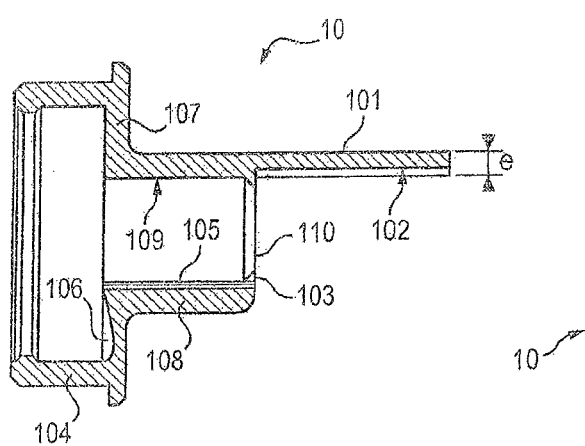
FIG. 6a, is a view in longitudinal section of the outer piece of FIG. 5.

The second rigid piece 10 illustrating the first embodiment, shown in FIGS. 5 and 6a, comprises at the level of a first end a base 104, open to the side of the first end. This base 104 is surmounted in the longitudinal direction by a hollow intermediate part 108, connected to the base 104 by a shoulder 107. For each dispensing chamber 22, on an inner face the shoulder 107 comprises a hollow 106 whereof an opening is oriented to the interior of the base 104 so as to also terminate in a conduit 105 arranged longitudinally on an inner wall 109 of the intermediate part 108. The intermediate part 108 terminates by an opening 103 forming a second end 110 of the second rigid piece 10 and at the level of which the conduit 105 terminates. The opening 103 and the conduit 105 connect each dispensing chamber 22 to the dedicated hollow 106. A rigid growth 101 extends longitudinally projecting from the second end 110. The growth 101 comprises an inner face 102 of concave semi-circular form. The growth can be of form in cross-section in an arc of a circle having a thickness E of between 0.5 and 1.5 mm. The growth 101 is located diametrically opposite relative to the conduit 105.

Figure 6B:
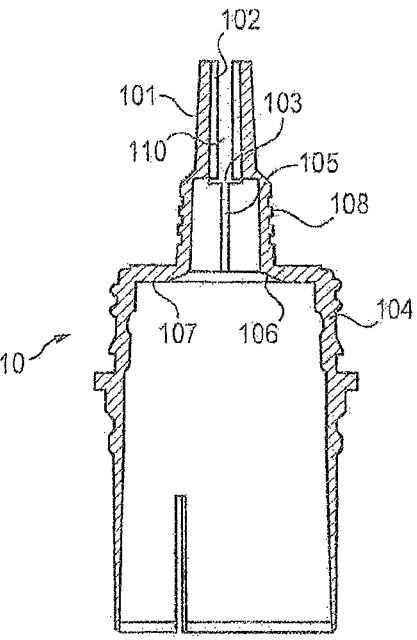
FIG. 6b is a view in longitudinal section of the outer piece forming a second rigid piece illustrating the second embodiment of the device according to the invention.

The second rigid piece 10 according to the second embodiment is illustrated in FIG. 6b. It has two rigid growths 101 extending longitudinally projecting from the second end 110. The growths 101 comprise an inner face 102 of concave semi-circular form. The growths 101 have a form in cross-section in an arc of a circle having a thickness E. The dosing chambers 22 extend into the two annular sections located between the growths 101. Longitudinal faces of width E of the growths 101 constitute walls of the dosing chambers 22.

Example of Assembly of the Dispensing Accessory

FIG. 1a shows an assembly of the dispensing accessory 7 illustrating a first embodiment of the device. Placed in the annular cavity of the shoulder 66 of the rigid core 6 is a first valve 5, here made of elastically deformable elastomer flexible material covered in a layer of parylene, covering the orifices 64. Next, the second rigid piece 10 is fitted to slide on the rigid core 6 such that the base 104 of the second rigid piece 10 covers the base 65 of the rigid core 6. Once in position, the first valve 5 is sandwiched between the shoulders 66 and 107 of the rigid core 6 and of the second rigid piece 10 respectively. In use, the first valve 5 can open by deformation in the hollow 106 of the second rigid piece 10, releasing a passage from at least one of the orifices 64 of the rigid core 6. The resulting fitting is tight, since the base 104 is complementary to the base 65, and therefore the intermediate part 108 of the second rigid piece is complementary to the first section 63 of the rigid core 6. Keeping the second rigid piece 10 and of the rigid core 6 in place is ensured by clipping, adhesion and/or welding.

The supple membrane 20 is then fitted to slide on the second section 62 of the rigid core 6 and the growth 101 of the second rigid piece 10, until the end 25 comes into contact on the second end 110 of the intermediate part 108 of the second rigid piece 10 and on an apex of the first section 63 of the rigid core 6. Therefore, the at least one dispensing chamber 22 is delimited by the part 21 of the supple membrane 20 and by a first portion 621 of the periphery of the second section 62. The surface 231 of the supple membrane is in contact with a second portion 622 of the periphery of the rigid core, second portion 622 complementary to the first portion 621. On the other hand, in the case illustrated here the supple membrane 20 is sandwiched longitudinally between the growth 101 of the second rigid piece 10, whereof the inner face 102 is supported on an outer surface of the supple membrane, and the second section 62 of the rigid core 6. So, the surface 231 of the supple membrane is in permanent contact with the second portion 622 of the periphery of the rigid core. Also, the inner face 102 can be glued or welded onto the outer surface of the supple membrane 20. So, the growth 101 extends over a distance equivalent to a longitudinal dimension of the dispensing chamber 22 and is located diametrically opposite said dispensing chamber. Also, the conduit 105 terminates in the dispensing chamber 22 to feed it following dispensing by said dispensing chamber of a dose or drop of product to be dispensed.

The dispensing accessory 7 assembled in this way is then mounted tightly on the opening of the container 8. Assembling the dispensing accessory 7 illustrating the second embodiment of the device is done equivalently to the particular features of the second rigid piece 10 and of the supple membrane 20. So the supple membrane 20 now covers the intermediate part 108 of the second rigid piece 10.

In the illustrations of the two embodiments of the device, at rest, the end 24 of the supple membrane 20 is a leaktight manner with a surface of the end 61 of the rigid core 6. When the part 21 of the supple membrane 20 is pressed, the product contained in the corresponding dispensing chamber 22 is put under pressure. Due to the presence of the first valve 5, the product to be dispensed cannot return to the enclosure of the container 8. The end 24 of the supple membrane deforms by unsticking from the surface of the end 61 of the rigid core 6, letting said product to be dispensed be dispensed. Once the product is expelled, the end 24 returns to the rest position on the end 61. Relaxing of pressure on the part 21 of the supple membrane 20 lets this part 21 return to the rest position, creating a depression in the dispensing chamber which tries to regain its rest form. As the contact between the end 24 of the supple membrane 20 with the end 61 of the rigid core forms a non-return valve (preventing air and outer contaminants from entering the dispensing chamber), the valve 5 opens to let the product to be dispensed pass through from the enclosure of the container 8 to the dispensing chamber 22 via the conduit 5.

Examples Illustrating Embodiments of the First and Second Valves

Examples of First Valve

The first valve 5 is made by a first moulding step of elastomer material, and by a second step for processing the valve with parylene to cover its surface with a coating of parylene, preferably parylene C.

The elastomer material can be silicone. The elastomer material can be thermoplastic elastomer with polyolefin base, such as ethylene-propylene-diene-monomer. The elastomer material can be styrene-based thermoplastic elastomer, for example styrene-butadiene or styrene-ethylene-butylene or styrene-ethylene-propylene. The material can be thermoplastic polyurethane.

The first valve 5 has a substantially plane general annular form of an outer diameter D whereof the value is for example between 11 and 20 mm, for example between 13 and 17 mm, for example 15 mm. The annular form of the first valve 5 is also delimited by an inner rim 53 of inner diameter d between 5 and 10 mm, for example between 6.5 and 8.5 mm, for example 7.5 mm. The thickness of the first valve 5 can be for example between 0.25 and 2.5 mm, for example 0.5 and 1.5 mm.

The form of the first valve 5 has at least one circumferential protuberance extending over at least one of the faces of the first valve 5.

The examples of first valve 5 shown in FIGS. 12a to 12g are adapted to allow passage of the product for ophthalmic use by deformation at the level of a central opening, an outer rim 52 of the valve 5 being held in position by forces applied to either side of the latter. Such operation is illustrated by the figures relative to the second embodiment.

Figure 12A:
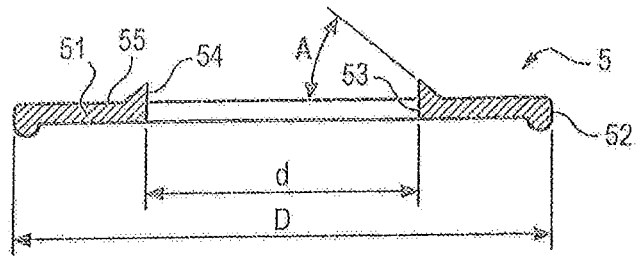

FIG. 12a illustrates an annular form 51 having a convex peripheral circumferential protuberance at the level of the outer rim 52 of the first valve 5, of maximal thickness of 0.5 mm, on a face of the first valve 5. The form also has a central circumferential protuberance at the level of the inner rim 53, of maximal thickness of 0.5 mm, on a face opposite the first valve 5. The outer diameter D is 15 mm. The inner diameter d is 7.5 mm. The thickness of the annular form 51 is 0.5 mm. The central circumferential protuberance comprises an annular surface 54 of an outer diameter D of 9 mm, at the periphery of which is an oblique annular transition area 55 having an angle A of 45° for example.

Figure 12B:
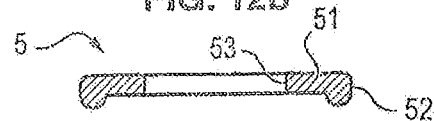

FIG. 12b illustrates an annular form 51 having just one convex peripheral circumferential protuberance at the level of the outer rim 52.

Figure 12C:
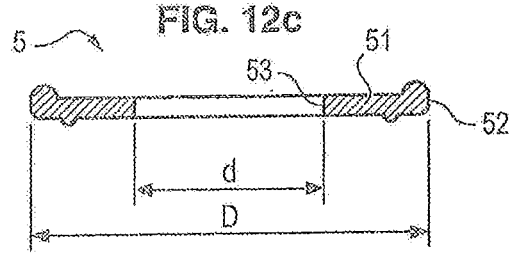

FIG. 12c illustrates an annular form 51 having convex a peripheral circumferential protuberance of 0.5 mm of radius extending over a face of the first valve 5, at the level of the outer rim 52, and a convex intermediate circumferential protuberance of 0.25 mm of radius extending over the face opposite the first valve 5, at a distance from the inner rim 53 and the outer rim 52.

Figure 12D:
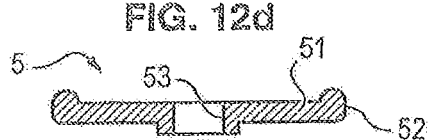

FIG. 12d illustrates an annular form 51 having a convex peripheral circumferential protuberance on a face of the first valve 5, at the level of the outer rim 52, and a central circumferential protuberance, at the level of the inner rim 53, on the face opposite the first valve 5.

Figure 12F:
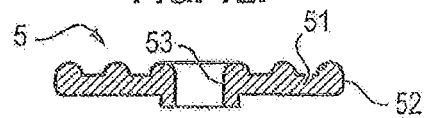
Figure 12E:
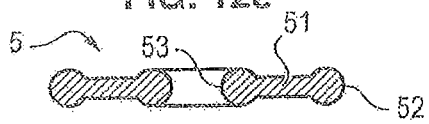

FIG. 12e illustrates an annular form 51 having a convex peripheral circumferential protuberance on the two faces of the first valve 5, at the level of the outer rim 52, and a central circumferential protuberance extending over the two faces of the first valve 5, at the level of the inner rim 53.

FIG. 12f illustrates an annular form 51 having a convex peripheral circumferential protuberance extending over a face of the first valve, at the level of the outer rim 52, a central circumferential protuberance extending over the two faces of the first valve 5, at the level of the inner rim 53, and a convex intermediate circumferential protuberance extending over a face of the first valve 5, at a distance from the inner rims 53 and outer rims 52.

Figure 12G:
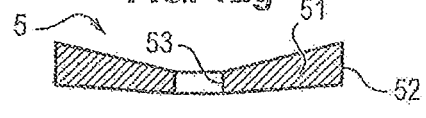

FIG. 12g illustrates an annular form 51 having an increasing thickness between the inner rim 53 and the outer rim 52.

Figure 12H:

The examples of the first valve 5 also shown in FIGS. 12a to 12g, as well as FIG. 12h are adapted to allow passage of the product by deformation of the outer rim 52, a central area of the first valve 5 at the level of the inner rim 53 being held in position by forces applied to either side of the latter.

FIG. 12h illustrates an annular form 51 of constant thickness whereof a profile at rest has an angle.

According to another example, the first valve 5 can have a hat shape, comprising a central cylindrical form, and a peripheral circumferential protuberance.

The dispensing accessory 7 can comprise a return element such as a spring to keep the first valve in a blocking position. According to such an example, the dispensing accessory 7 does not necessarily have a dispensing chamber.

Examples of Second Valve

FIG. 1b shows an example of air intake and filtration means illustrating the second embodiment of the device. The air passes via an opening of the base 4, and crosses a tubular filter 41. At the outlet of the filter 41 is a cylindrical chamber 42 whereof an opening is closed by a central area of a second valve 3 comprising elastomer material, covered in a layer of parylene.

The elastomer material can be silicone. The elastomer material can be thermoplastic elastomer with polyolefin base, such as ethylene-propylene-diene-monomer. The elastomer material can be styrene-based thermoplastic elastomer, for example styrene-butadiene or styrene-ethylene-butylene or styrene-ethylene-propylene. The material can be thermoplastic polyurethane.

The second valve 3 lets outside air enter the container 8 when the supple membrane 20 of the dispensing accessory 7 is relaxed without letting the product or substantially the air contained inside the container 8 exit when the supple membrane 20 is stressed.

The second valve 3 has a substantially plane general circular form delimited by an outer rim and is adapted for passage of the product by deformation at the level of a central opening, the outer rim of the second valve 3 being kept in position by forces applied to either side of the latter. The outer rim is fitted with teeth or slots. When the central area of the second valve 3 deforms, the air located in the chamber 42 can enter a second annular chamber 43 located at the periphery of the first chamber 42. This chamber 43 is directly connected inside the container 8 by the interstices between the teeth of the outer rim or the slots of the outer rim.

Alternatively, the second valve 3 can enable passage of the filtered outside air by deformation of the outer rim, the central area of the valve 3 being kept in position by forces applied on either side of the latter. In this case, the first chamber 42 is substantially annular.

Figure 13A:
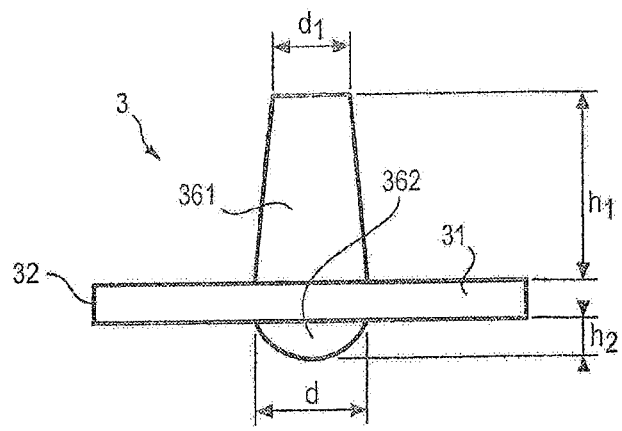
Figure 13B:
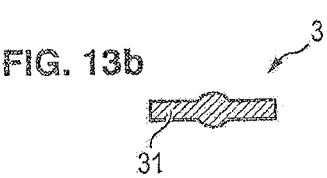
Figure 13E:
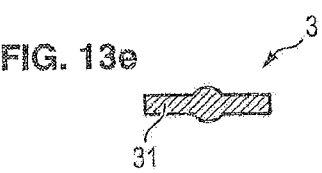
Figure 13C:
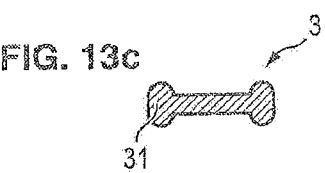

FIGS. 13a to 13c illustrate examples of a second valve 3 for passage of air by deformation of the central area of the second valve 3.

The second valve 3 illustrated in FIG. 13a has a form constituted by a circular form 31 and a protuberance 361 and 362. The circular form 31 is substantially plane and has two faces, a first face and a second face. The first face is turned towards the interior of the container 8. The circular form 31 is delimited by an outer diameter D. The outer diameter D can assume a value for example between 3 and 9 mm. The outer diameter D can assume a value for example between 5 and 6 mm, for example 5.70 mm. The protuberance extends over a central area of the circular form 31 defined by an inner diameter d. The inner diameter d can assume a value of between 1 and 3 mm, for example 1.5 mm. The protuberance engaged with the circular form 31, extending perpendicularly to the circular form 31 on either side of the circular form 31 in a first protuberance 361 engaged with the first face and a second protuberance 362 engaged with the second face. The first protuberance 361 has a circular cross-section. It can have a height h1 of between 1 and 5 mm, for example between 2 and 3 mm, for example 2.5 mm. The end of the first protuberance can comprise a circular surface of diameter dl of between 0.5 and 1 mm, for example 1 mm. The second protuberance 362 can be convex, of height h2 of between 0.25 and 1 mm, for example 0.5 mm.

FIG. 13b illustrates an example of a second valve 3 which has a first protuberance 361 and a second protuberance 362, both of convex form.

FIG. 13c illustrates an example of a second valve 3 of circular form having on each face a convex circumferential protuberance at the level of the outer rim.

Figure 13F:
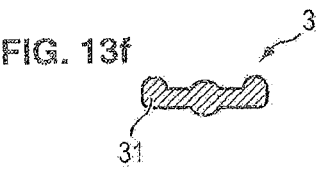
Figure 13D:
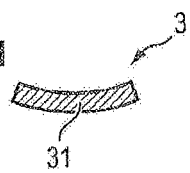

FIG. 13d illustrates an example of a second valve 3 having at rest a curve profile, in the form of an arc of a circle, with the first face being convex to the side of the curve and the second face being concave to the side of the curve.

Figure 13G:
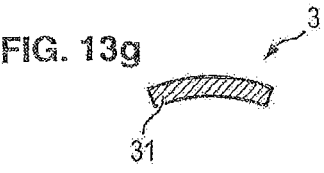

FIGS. 13e to 13g illustrate examples of a second valve 3 for passage of air by deformation of the outer rim of the second valve 3.

FIG. 13e illustrates an example of a second valve 3 which has a first protuberance 361 and a second protuberance 362, both of convex form.

FIG. 13f illustrates an example of a second valve 3 which has a first protuberance 361 and a second protuberance 362, both of convex form, and on each face a convex circumferential protuberance at the level of the outer rim.

FIG. 13g illustrates an example of a second valve 3 having at rest a curve profile, in the form of an arc of a circle, with the first face being concave to the side of the curve and the second face being convex to the side of the curve.

Treatment by Parylene

Analyses have shown strong interaction between the analogs of prostaglandin and the components of dispensing devices for packaging and dispensing of calibrated drops of a product for ophthalmic use.

It has been shown by tests that strong interaction affected valves made of silicone elastomer and prostaglandin analogs. The applicant has noted that the interaction was characterized by adsorption or absorption of prostaglandin by the elastomer, silicone in particular.

As illustrated in FIGS. 14a to 14c and 15a to 15c, it has been observed that poly-p-xylylene or parylene treatment, consisting coating the elastomer valves with a layer of parylene resolved this problem posed by the silicone or fluorosilicone membranes. Parylene has thin-layer and biocompatible tightness properties.

This observation results from analyses by high-performance liquid chromatography performed on ophthalmic solutions based on Latanoprost. Analysis involve apparatus comprising a LACHROM ELITE system. The apparatus comprises L2130 pumps, a L2300 oven, a L2200 injector, a L2400 detector and LACHROM ELITE software. The column is Nucleosil 100-5-C18 type (125×4)-5 µm Ref MN 721622-40. The eluant consists of KH2PO4 0.05 M (6.8 g/l) adjusted to pH=3 with H3PO4 (for 50 V) and acetonitrile (for 50 V). The rate is 1.0 mL·min−1. Detection is at a level of 210 nm. The injected volume is 5 µL. The retention time for the Latanoprost is around 4.4 minutes.

Figure 14A:
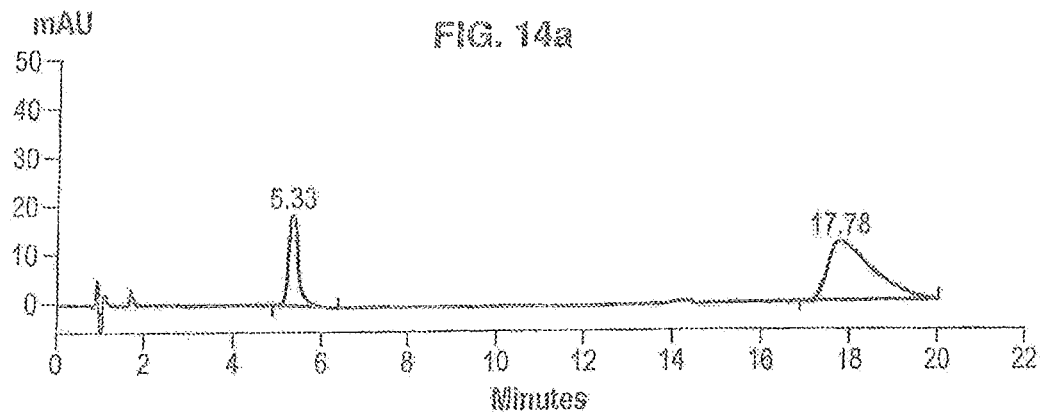
Figure 14B:
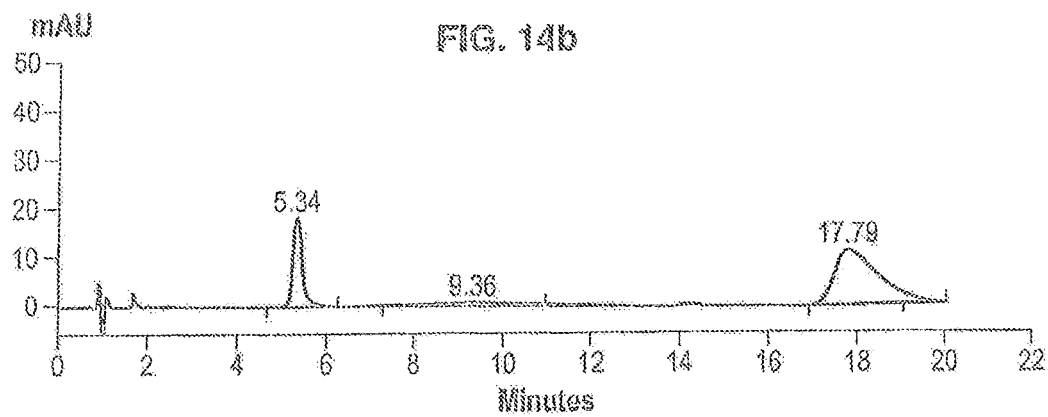
Figure 14C:
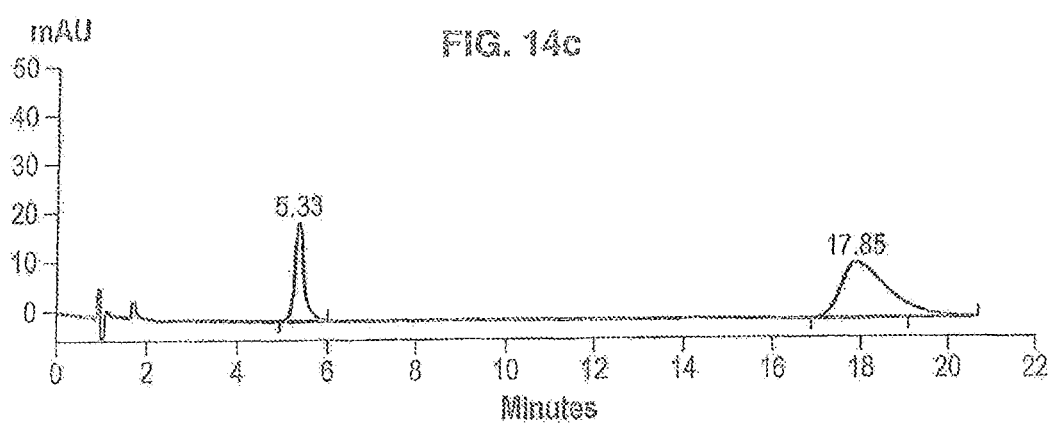
Figure 15A:
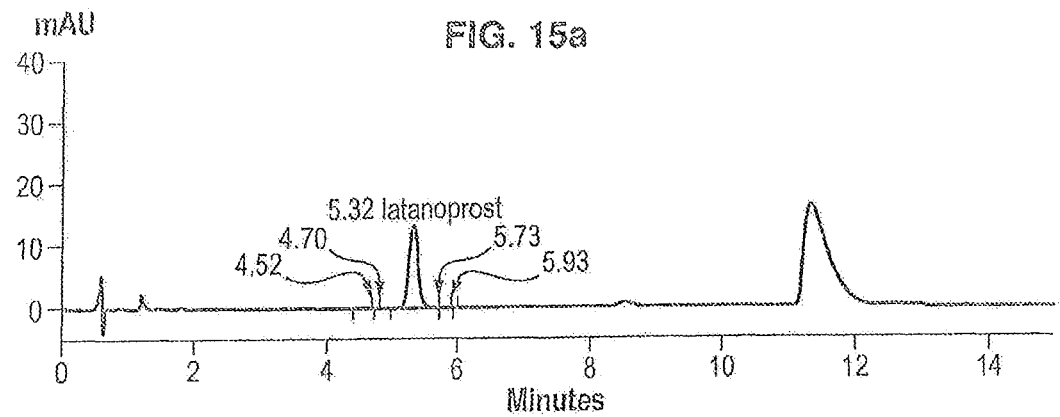
Figure 15B:
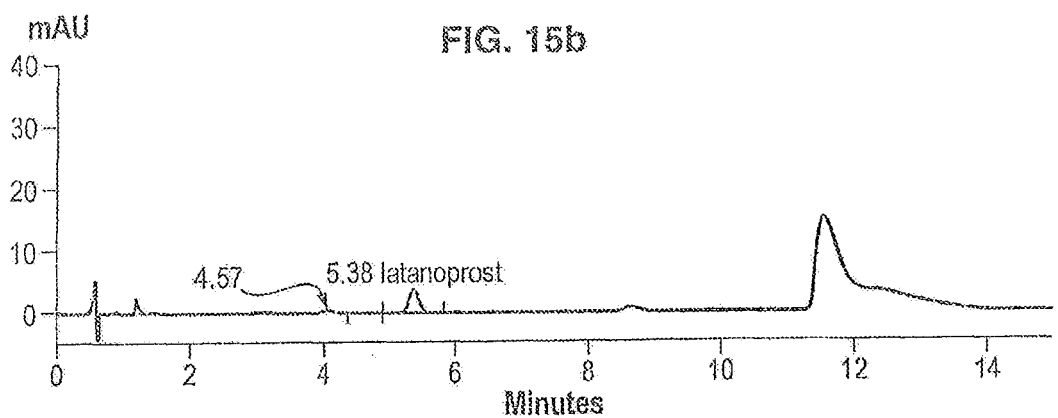
Figure 15C:
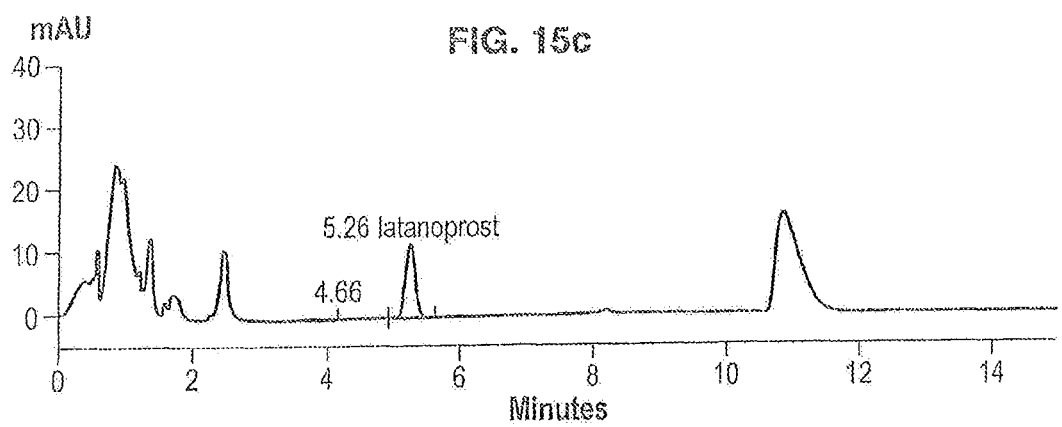

FIG. 14a, respectively 14b and 14c show chromatography measurement in the initial state presenting a Latanoprost solution, respectively a Latanoprost solution and a matrix of elements of elastomer valve according to the prior art, and a Latanoprost solution and a matrix of elements of elastomer valve covered in a layer of parylene. The characteristic peak of Latanoprost is at 5.34 minutes. FIGS. 15a, 15b and 15c show the results of analysis by high-performance liquid chromatography of the same solutions after thirty days. The results of analyses of solutions tested by high-performance liquid chromatography in terms of Latanoprost content in ppm initially, at ten days and at thirty days, are consigned in table 1.

TABLE 1

| | T = 0 | T = 10 days | T = 30 days |
|---|---|---|---|
| Latanoprost + matrix prior art | 48.1 ppm | 24.2 ppm | 15.2 ppm |
| Latanoprost + matrix treated with parylene | 49.4 ppm | 48.2 ppm | 45.1 ppm |

Parylene processing resolves similar problems of interactions between the valves and some corticoids and some non-steroidal anti-inflammatories which the product for ophthalmic use of the device can contain.

The valves described in document FR 2873358 have circular and perfectly flat forms. They have no curvature, angle, or protuberance. These valves pose problems of tightness of the device. Also, these valves adhere together strongly and become attached to each other, posing industrialisation problems, in particular in terms of their storage and handling. The presence of reliefs and non-flat forms difficult to fit are examples of forms not having such disadvantages. Subsequent parylene treatment also diminishes the silicone adherence properties.

Parylene processing resolves similar problems of interactions between a product for ophthalmic use and the valves made of another elastomer material such as thermoplastic elastomer with polyolefin base, for example ethylene-propylene-diene-monomer, or styrene-based thermoplastic elastomer, for example styrene-butadiene or styrene-ethylene-butylene or styrene-ethylene-propylene, or thermoplastic polyurethane.

Parylene processing also diminishes the adherence properties of these elastomers.

Examples of Embodiments of the Dispensing Chamber

The fact that the dispensing accessory 7 comprises means for keeping (growth 101, respectively growths 101 of the second rigid piece 10 of the device illustrating the first, respectively second, embodiment of the invention) the supple membrane 20 in permanent contact with the second portion 622 of the periphery of the rigid core 6 ensures that the entire volume of product contained in the dispensing chamber 22 is properly ejected towards the end 61 of the rigid core 6, which acts as dispensing nozzle. In fact, crushing a cylinder of elastomer material involves its deformation, augmentation in the radial direction of the initial radius. Because tightness is necessary for expulsion of the liquid located in the dispensing chamber, any leak causes malfunction of the system. In this case, if the membrane were not kept in contact with the rigid core, as indicated hereinabove, pressing on the part 21 of said membrane would result in deformation of the membrane (under the effect of crushing and rise in pressure of the product present in the chamber) which would then move away from the second portion 622 of the periphery: some of the product dose to be dispensed contained in the dispensing chamber would infiltrate the resulting interstice and would not be expelled at the level of the end 24 of the supple membrane 20. An incorrect dose would then be supplied to the patient. The growth 101 of the second rigid piece 10, located in opposition to the dispensing chamber 22, limits these deformations.

Figure 7:
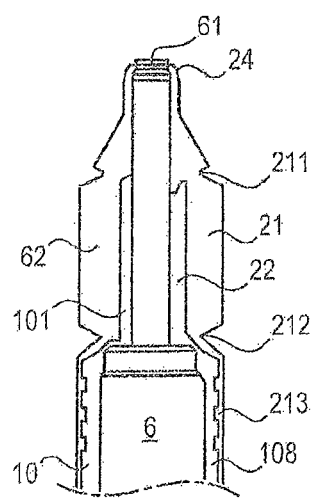
FIG. 7 is a partial view in longitudinal section illustrating a variant of the second embodiment of the device according to the invention.

FIG. 7 illustrates a variant of the second embodiment of the device, this variant comprising characteristics of devices illustrating the first embodiment, in that it comprises only a single growth 101. Here, the second rigid piece 10 is inside the supple membrane 20 which when mounted is fitted on the rigid core 6 and on the second piece 10. The supple membrane 20 comprises a skirt 213 covering the intermediate part 108 of the second piece 10. The single growth 101 is sandwiched between the supple membrane 20 and the second section 62 of the rigid core 6. The supple membrane 20 is glued or welded onto an outer surface of the growth 101, disallowing it to deform during use.

In another variant embodiment, the supple membrane is at least overmoulded onto the growth 101 of the second rigid piece.

Figure 8:
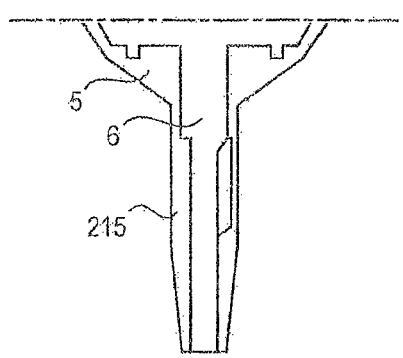
FIG. 8 is a partial view in longitudinal section of a dispensing accessory illustrating a third embodiment of a device according to the invention.

In a third embodiment of a device, illustrated in FIG. 8 and whereof the only differences from the first embodiment will be described, the dispensing accessory 7 comprises no second rigid piece 10. The supple membrane 20 is directly fitted onto the rigid core 6, trapping the valve 5 in the base of the rigid core. Deformation of the supple membrane 20 is prevented during dispensing use, by adhesion or welding of the part 215 of the supple membrane 20 onto the second portion 622 of the periphery of the rigid core 6.

From an ergonomic point of view, documents of the prior art disclose considerable imprecision of the gesture which causes either touching the ocular surface with the end of the nozzle, therefore the risk of contamination of the latter, or not reaching the ocular surface, resulting in poor observance of treatment. The force necessary to actuate it can also be an added disadvantage.

Figure 9A:
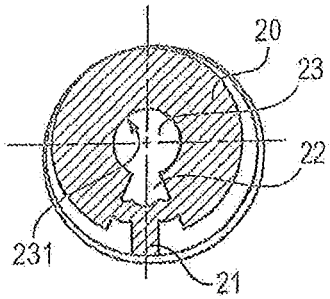
FIG. 9a, is a view in section according to a section of the supple membrane of FIG. 3a, at the level of the dispensing chamber.
Figure 9B:
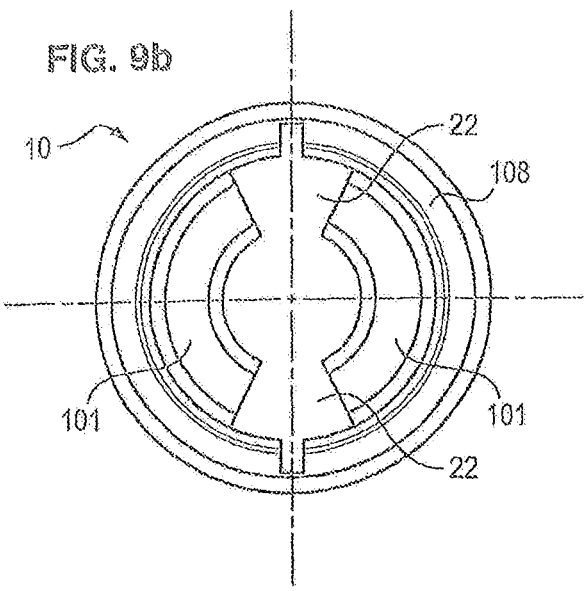
FIG. 9b is a sectional view according to a section of the dispensing accessory illustrating the second embodiment of the device according to the invention.

FIGS. 9a and 9b illustrate the operation of each dispensing chamber 22. Due to the elastomer nature of the supple membrane 20, the cross-sectional form of the dispensing chamber 22 is generally trapezoid, giving the dispensing chamber 22 the form of a prism, so the part 21 of the supple membrane 20 has a general prismatic form which, during pressing, optimally fills the dispensing chamber 22. This form has more advantage, in its operation, of being independent of the viscosity of the product to be dispensed from said chamber, and offers minimal deformation of the part 21. During pressing, the interval between the part 21 outer to the prism forming the dispensing chamber 22 and said dispensing chamber 22 reduces, effectively increasing the shearing of the product to be dispensed contained in the dispensing chamber 22, therefore expelling viscous liquids, the viscosity of which depends on the shear rate. Some pharmaceutical products are viscous solutions the viscosity of which depends on the shear rate, for example a composition whereof the law of viscoelastic behaviour decreases as a function of the intensity of shear and the aim of which is to reproduce the behaviour of the lachrymal viscosity fluid high at rest and low under the influence of shear, caused for example by the blinking of eyelids, inversely to fluids of Newtonian type of constant viscosity.

For Newtonian fluid, the viscosity will remain constant, irrespective of the shear rate, so the force used to evacuate the product from the dispensing chamber 22 will be proportional to the chamber surface in contact with the liquid, that is, high at the start of pressing and trailing off progressively in relation to the surface in contact.

Inversely, when the product for ophthalmic use is rheofluidifying fluid, of high viscosity with low shear, as described by EP0698388 in the case of a hyaluronic solution intended for artificial tears, this force will be even higher at the start of pressing, and a dispensing chamber 22 diminishing this initial force should therefore be proposed.

Figure 10A:
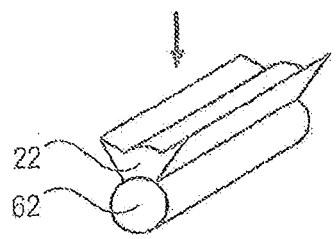
FIGS. 10a to 10c are diagrams showing deformation of a dispensing chamber of the dispensing accessory illustrating the device according to the invention.
Figure 10B:
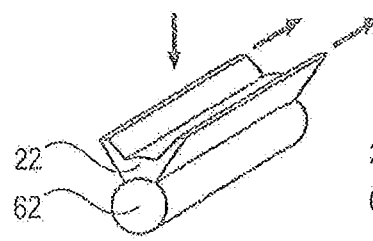
Figure 10C:
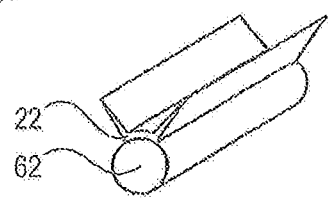

For a dispensing chamber 22 comprising a fixed part and a mobile part, the contact point area between the fixed part and the mobile part is in the form of an airgap widening progressively between the thickness zero at the point of contact and a given thickness, preferably low. In this way, during stress A of the mobile part the liquid will be shorn the most strongly around the point of contact, therefore will be lower in viscosity and will flow E preferably into this area. This is illustrated in FIGS. 10a to 10c.

Therefore, in the first and second embodiments of the device the supple membrane 20, at least at the level of its portion constituting at least one part of the dispensing chamber 22, is made of elastomer material, deforming under the action of pressing A, and in the same way having an area of lesser thickness at the level of contact between the mobile part and the fixed part, and of general prismatic form.

The form given to the part 21 filling the dispensing chamber 22 can assume several variants illustrated in non-limiting manner by FIGS. 11a to 11c. These examples retain the notion of a distance reducing progressively, subjecting only some of the liquid to a high shear rate and enabling its flow preferably in the high shear area and not in the entire dispensing chamber 22.

FIG. 11a schematically illustrates a flat bevelled form on the exterior of the part 21a filling the dispensing chamber 22a.

FIG. 11b schematically illustrates a wedge form of the part 21b filling the dispensing chamber 22b.

FIG. 11c schematically illustrates a rounded convex form of the part 21c filling the dispensing chamber 22c.

The invention claimed is:

1. A device for packaging and dispensing drops of a product for ophthalmic use, fluid, semifluid or in suspension, emulsion or oily solution, comprising a dispensing accessory comprising a first valve made of elastomer material allowing passage of the product when the dispensing accessory is stressed without allowing outside air to move in a reverse direction when the dispensing accessory is relaxed, wherein the first valve is covered with a layer of parylene,
   wherein the dispensing accessory is a dispensing accessory for calibrated drops comprising:
      a supple membrane whereof a stress causes dispensing of the product,
      a dispensing chamber of the product delimited at least by:
         a first portion of a periphery of a rigid core and
         a part of elastically deformable flexible membrane located facing the first portion, the flexible membrane extending about the rigid core,
      the first valve made of elastomer material allowing the product to enter the dispensing chamber when the supple membrane is stressed without allowing outside air to move in the reverse direction when the supple membrane is relaxed,
      wherein the device comprises form-holding means of the supple membrane, relative to at least one second portion of the periphery of the rigid core, the form-holding means comprising:
         at least one rigid piece attached to the supple membrane and extending opposite the second portion of the periphery of the rigid core, the rigid piece being located between the supple membrane and the second portion of the periphery of the rigid core, or
         a rigid piece attached to a part of the supple membrane extending opposite the second portion of the periphery of the rigid core, the part of the supple membrane being located between the rigid piece and the second portion of the periphery of the rigid core, or
         an assembly of the supple membrane with a surface of the second portion of the periphery of the rigid core by adhesion or welding.

2. The device according to claim 1, comprising:
   a container intended to contain the product and dispense it, the dispensing accessory being mounted on the container and the first valve allowing the product to exit the container when the dispensing accessory is stressed without allowing outside air to enter the container when the dispensing accessory is relaxed,
   a renewal and filtration assembly of the air entering the container after dispensing of a product portion or dose, comprising a second valve made of elastomer material and covered with a layer of parylene, allowing outside air to enter said container when the dispensing accessory is relaxed without allowing the product or substantially the air contained inside the container to exit when the dispensing accessory is stressed.

3. The device according to claim 2, wherein the second valve has a form comprising:
   a substantially plane circular form having two faces, a first face being turned towards the interior of the container and delimited by an outer rim, and a protuberance extending over a central area of the circular form delimited by an inner diameter, engaged with the circular form, extending perpendicularly to the circular form on either side of the circular form.

4. The device according to claim 1, wherein the first valve has a hat shape, comprising:
a central cylindrical form, and
a peripheral circumferential protuberance.

5. The device according to claim 2, wherein the first valve has a substantially plane circular shape delimited by an outer rim and is adapted to allow passage of the product:
by deformation at the level of a central area, the outer rim of the first valve being held in position by forces applied on either side of the first valve, or
by deformation of the outer rim, a central area of the valve being held in position by forces applied on either side of the first valve.

6. The device according to claim 5, wherein a thickness of the first and/or second valve(s) increases between the central area and the outer rim.

7. The device according to claim 5, wherein the first and/or second valve(s) at rest has a curve profile and/or has at least one angle.

8. The device according to claim 5, wherein the form of the first and/or second valve(s) has at least one circumferential protuberance extending over at least one face of the first and/or of the second valve(s).

9. The device according to claim 5, wherein the first valve has a substantially plane annular form delimited by:
an inner diameter between 5 and 10 mm and
an outer diameter of between 11 and 20 mm,
the outer diameter having a thickness of between 0.25 and 2.5 mm.

10. The device according to claim 2, wherein the elastomer material of the first and/or second valve(s) is silicone.

11. The device according to claim 2, wherein the elastomer material of the first and/or second valve(s) is thermoplastic elastomer with polyolefin base, or styrene-based thermoplastic elastomer or thermoplastic polyurethane.

12. The device according to claim 1, wherein:
the dispensing chamber has a general trapezoid form in cross-section, and/or
the part of the supple membrane delimiting the dispensing chamber forms a generally prismatic piece which comprises two ends each having an area of lesser thickness.

13. Use of the device according to claim 1, comprising:
packaging a product for ophthalmic use in the device according to claim 1; and
dispensing drops of the product for ophthalmic use from the device according to claim 1,
wherein the product for ophthalmic use comprises an analog of prostaglandin.

14. Use of the device according to claim 1, comprising:
packaging a product for ophthalmic use in the device according to claim 1; and
dispensing drops of the product for ophthalmic use from the device according to claim 1,
wherein the product for ophthalmic use comprises a corticoid.

15. Use of the device according to claim 1, comprising:
packaging a product for ophthalmic use in the device according to claim 1; and
dispensing the product for ophthalmic use from the device according to claim 1,
wherein the product for ophthalmic use comprises a non-steroidal anti-inflammatory.

16. Manufacturing process of a device according to claim 2, wherein it comprises:
moulding a first and/or second valve(s) made of elastomer,
parylene processing of the first and/or second valve(s) made of elastomer for covering its surface with a coating of parylene,
mounting of the device with the resulting first and/or second valve(s).

17. A device for packaging and dispensing drops of a product for ophthalmic use, fluid, semi-fluid or in suspension, emulsion or oily solution, comprising a dispensing accessory comprising a first valve made of elastomer material allowing passage of the product when the dispensing accessory is stressed without allowing outside air to move in the reverse direction when the dispensing accessory is relaxed, wherein the first valve is covered with a layer of parylene,
wherein the dispensing accessory is a dispensing accessory for calibrated drops comprising:
a supple membrane whereof a stress causes dispensing of the product,
a dispensing chamber of the product delimited at least by:
a first portion of a periphery of a rigid core and
a part of elastically deformable flexible membrane located facing the first portion, the flexible membrane extending about the rigid core,
the first valve made of elastomer material allowing the product to enter the dispensing chamber when the supple membrane is stressed without allowing outside air to move in the reverse direction when the supple membrane is relaxed,
wherein
the dispensing chamber has a general trapezoid form in cross-section, and/or
the part of the supple membrane delimiting the dispensing chamber forms a generally prismatic piece which comprises two ends each having an area of lesser thickness.

\* \* \* \* \*